(12) United States Patent
Livie et al.

(10) Patent No.: US 11,771,211 B2
(45) Date of Patent: Oct. 3, 2023

(54) BEVERAGE CAN CLEANING DEVICE

(71) Applicants: Barbara Jean Livie, Clareholm (CA); Scott Alan Livie, Clareholm (CA)

(72) Inventors: Barbara Jean Livie, Clareholm (CA); Scott Alan Livie, Clareholm (CA)

( * ) Notice: Subject to any disclaimer, the term of this patent is extended or adjusted under 35 U.S.C. 154(b) by 149 days.

(21) Appl. No.: 17/187,855

(22) Filed: Feb. 28, 2021

(65) Prior Publication Data
US 2022/0273093 A1  Sep. 1, 2022

(51) Int. Cl.
| | | |
|---|---|---|
| *A46B 11/00* | (2006.01) | |
| *B08B 1/00* | (2006.01) | |
| *A46B 1/00* | (2006.01) | |
| *B08B 1/04* | (2006.01) | |
| *B65D 25/24* | (2006.01) | |
| *A61L 2/18* | (2006.01) | |
| *A61L 101/34* | (2006.01) | |

(52) U.S. Cl.
CPC ............ *A46B 11/0062* (2013.01); *A46B 1/00* (2013.01); *A61L 2/18* (2013.01); *B08B 1/002* (2013.01); *B08B 1/04* (2013.01); *B65D 25/24* (2013.01); *A46B 2200/3073* (2013.01); *A46B 2200/3093* (2013.01); *A61L 2101/34* (2020.08); *A61L 2202/17* (2013.01); *A61L 2202/23* (2013.01)

(58) Field of Classification Search
CPC ........ A46B 2200/3073; A46B 11/0062; B65D 23/12; B08B 1/00; B08B 1/001; B08B 1/002
See application file for complete search history.

(56) References Cited

U.S. PATENT DOCUMENTS

| | | | | |
|---|---|---|---|---|
| 3,641,610 A | * | 2/1972 | Lewis, Jr. ............... | A46B 3/20 401/268 |
| 4,763,380 A | * | 8/1988 | Sandvick ............ | A46B 11/063 D4/130 |
| 4,813,091 A | * | 3/1989 | Glasener ............... | B65D 25/20 D4/130 |
| 5,704,723 A | * | 1/1998 | Salisian ................... | A47K 7/03 401/8 |
| 2008/0035172 A1 | * | 2/2008 | Mindrum ............... | A47L 17/04 15/160 |
| 2015/0210465 A1 | * | 7/2015 | Raad ................... | B65D 47/122 220/592.16 |

\* cited by examiner

*Primary Examiner* — Natasha N Campbell
(74) *Attorney, Agent, or Firm* — CAPEHART LAW FIRM

(57) ABSTRACT

A device for cleaning a top of a beverage can. The device includes a main-body and a cleaning-member. The cleaning-member is saturated with a cleaning composition. The cleaning composition includes an amount of sanitizer or disinfectant such as alcohol, sufficient to at least reduce, if not kill or inactivate, pathogenic matter located on the top of the beverage can.

14 Claims, 8 Drawing Sheets

BEVERAGE CAN CLEANING DEVICE

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

TECHNICAL FIELD

The present invention relates generally to the field of cleaning devices of existing art and more specifically relates to a portable cleaning device for a top of a beverage can.

RELATED ART

A wide variety of beverages such as sodas and beer are sold in beverage cans. These cans have a top wall having an open-able mouth for dispensing the contents of the can. Often, the contents of the beverage can are consumed directly from the can, without being poured into a glass or cup. This is a problem as the top wall of beverage cans are easily contaminated during transportation, storage and even during use of the beverage can. As the top of the beverage will inevitably come into contact with the mouth of a consumer, it is important that the beverage can is free from contamination, particularly from pathogenic matter that can cause the individual to become sick.

Currently, individuals can wipe the can with a tissue or cloth. However, this is not ideal as tissues may not always be immediately available for the individual, and nevertheless, tissues/cloths do not sanitize or disinfect the can. Therefore, pathogenic matter is still left living on the can. Thus, a suitable solution is desired.

SUMMARY OF THE INVENTION

In view of the foregoing disadvantages inherent in the cleaning device art, the present disclosure provides a novel beverage can cleaning device. The general purpose of the present disclosure, which will be described subsequently in greater detail, is to provide a means of quickly and easily cleaning, sanitizing and/or disinfecting a top of a beverage can and thereby at least reducing, if not killing or inactivating, pathogenic matter thereon.

A device for cleaning a top of a beverage can is disclosed herein. The top of the beverage can including a top-wall having an open-able mouth section therein, and an upwardly extending circumferential lip bordering the top-wall. The device includes a main-body and a cleaning-member. The main-body may include a plate and a bordering-wall defining an interior and may be sized to encompass the top of the beverage can. The cleaning-member may be removably seated within the interior. The cleaning-member may include an inner-section and an outer-section. The inner section may be sized and configured to effectively clean the top-wall of the beverage can and the outer-section may be sized and configured to clean an outer surface and an inner surface of the circumferential lip of the beverage can. At least one of the inner-section and the outer-section may be saturated with a cleaning composition.

According to another embodiment, a method of using a device for cleaning a top of a beverage can is also disclosed herein. The method includes providing the device as above; placing the main-body over the top of the beverage can, the cleaning-member being seated therewithin; selectively pushing and twisting the main-body over the top of the beverage can, thereby: cleaning the top-wall of the beverage can with the inner-section of the cleaning-member and cleaning the outer surface and the inner surface of the circumferential lip of the beverage can with the outer-section of the cleaning-member; and removing the device from the top of the beverage can to drink a contents thereof.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a beverage can cleaning device, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to a cleaning device and more particularly to a beverage can cleaning device as used to clean, sanitize and/or disinfect a top of a beverage can, thereby at least reducing, if not killing or inactivating, pathogenic matter such as viruses, bacteria, fungi, or the like.

Generally disclosed is a cleaning device for removable attachment to a top of a beverage can and for cleaning the top of the beverage can. The cleaning device may act as a lid for the beverage can and may be attached thereto via a snap fastener. An interior of the cleaning device may include an alcohol saturated, absorbent, cleaning pad that may be used to clean the top of the beverage can, particularly a rim thereof and a mouth-section thereof. In some embodiments, a beverage can holder may be provided for attaching the cleaning device thereto. In some other embodiments, the cleaning device may include a keychain for fastening the cleaning device to keys.

Referring now more specifically to the drawings by numerals of reference, there is shown in FIGS. 1-9, various views of a device for cleaning a top of a beverage can ("device" 100).

Figure 1:
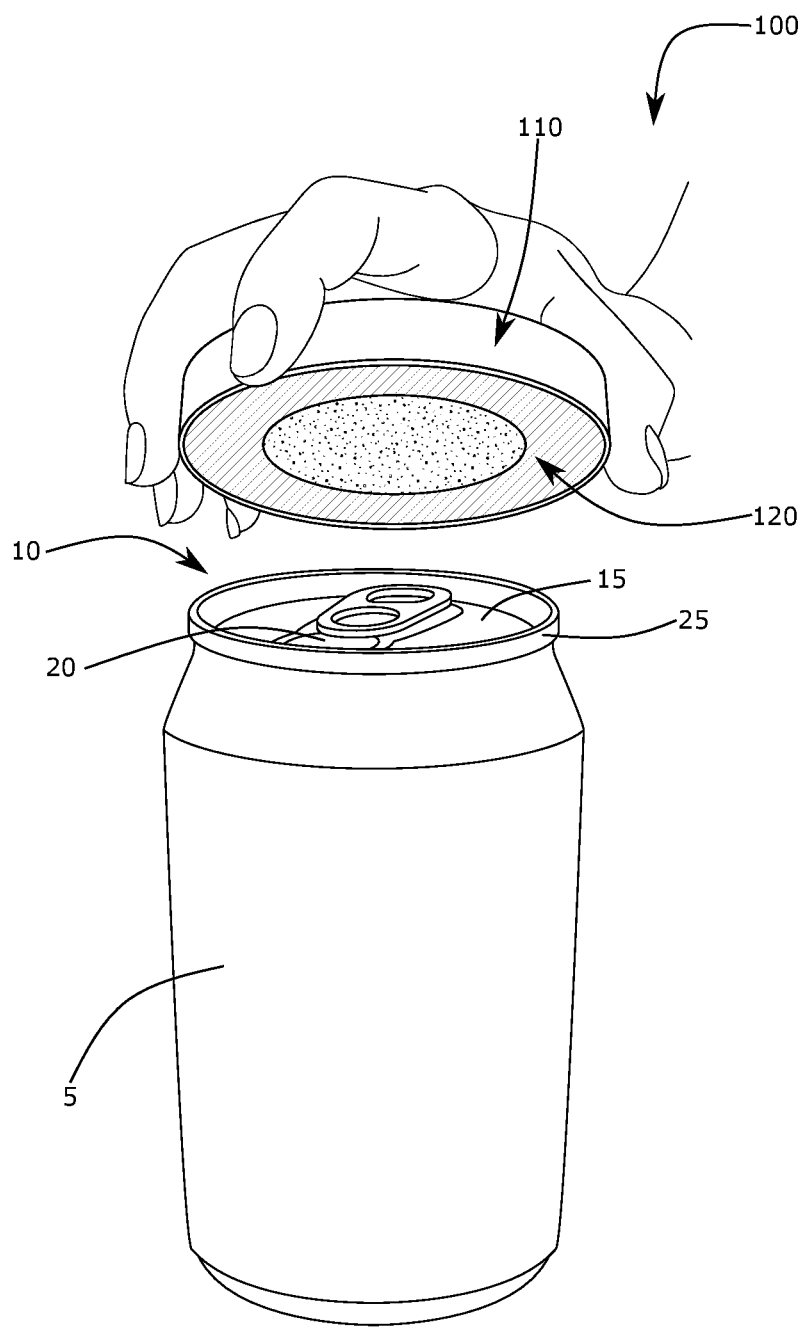
FIG. 1 is a perspective view of a device during an 'in-use' condition, according to an embodiment of the disclosure.

FIG. 1 shows a device 100 according to an embodiment of the present disclosure. As illustrated, the device 100 may include a main-body 110 and a cleaning-member 120. As shown, the device 100 may be used for cleaning a top 10 of a beverage can 5. The top 10 of the beverage can 5 may include a top-wall 15 having an open-able mouth-section 20 therein, and an upwardly extending circumferential lip 25 bordering the top-wall 15.

Referring now to FIGS. 2-9 showing various views of the device 100 of FIG. 1, according to an embodiment of the present disclosure. The main-body 110 may include a plate 112 and a bordering-wall 114 defining an interior 115. The main-body 110 may be sized to encompass the top 10 of the beverage can 5. Preferably, as shown, the main-body 110 may include a substantially cylindrical profile to match the beverage can 5. The main-body 110 may include a body-diameter 111 slightly larger than a can-diameter 45 of the top 10 of the beverage can 5 to aid the main-body 110 in fully encompassing the top 10 of the beverage can 5 and therefore aid in placing the cleaning-member 120 in contact with the top 10 of the beverage can 5.

Figure 2A:
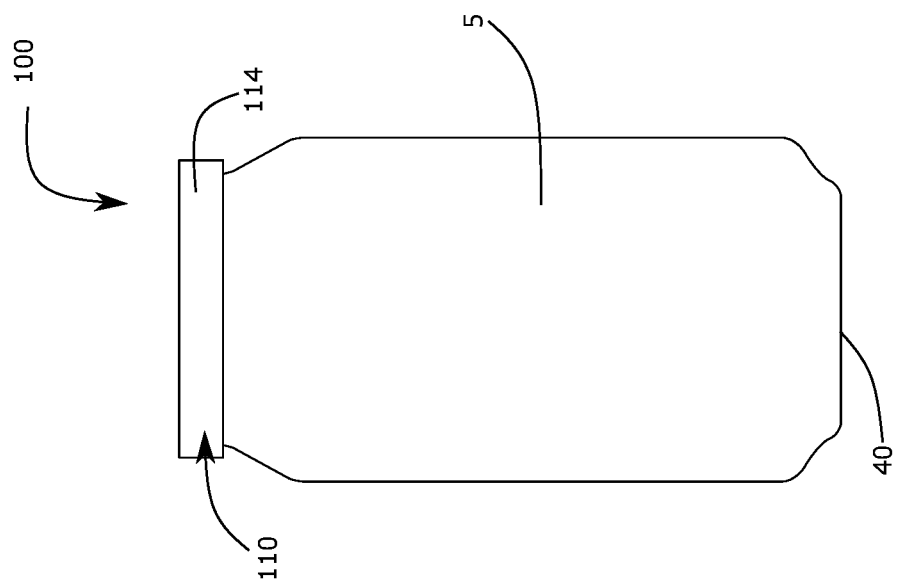
FIG. 2A is a front view of the device of FIG. 1, illustrating the device above a top of a beverage can, according to an embodiment of the present disclosure.
Figure 2B:
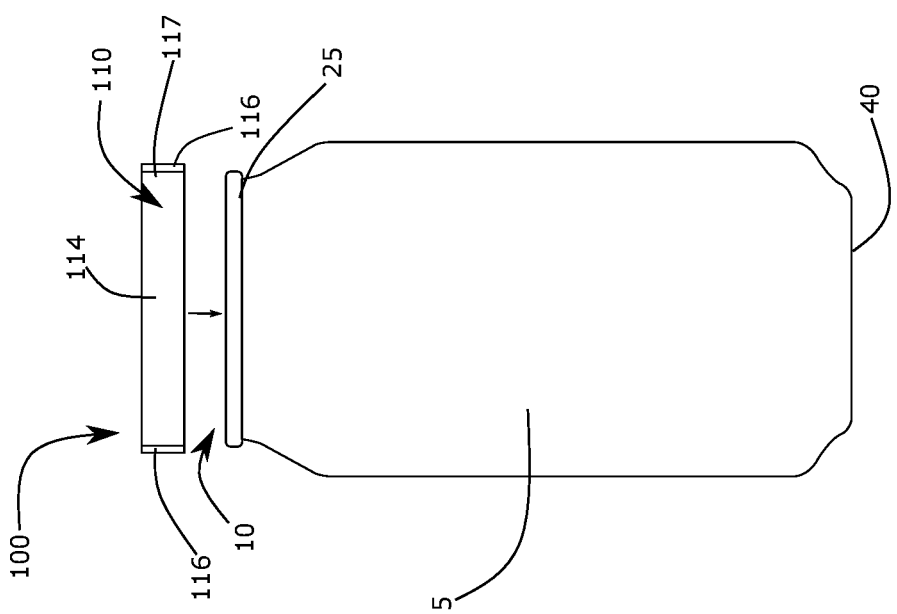
FIG. 2B is a front view of the device of FIG. 2A, illustrating the device attached to the top of the beverage can, according to an embodiment of the present disclosure.
Figure 3:
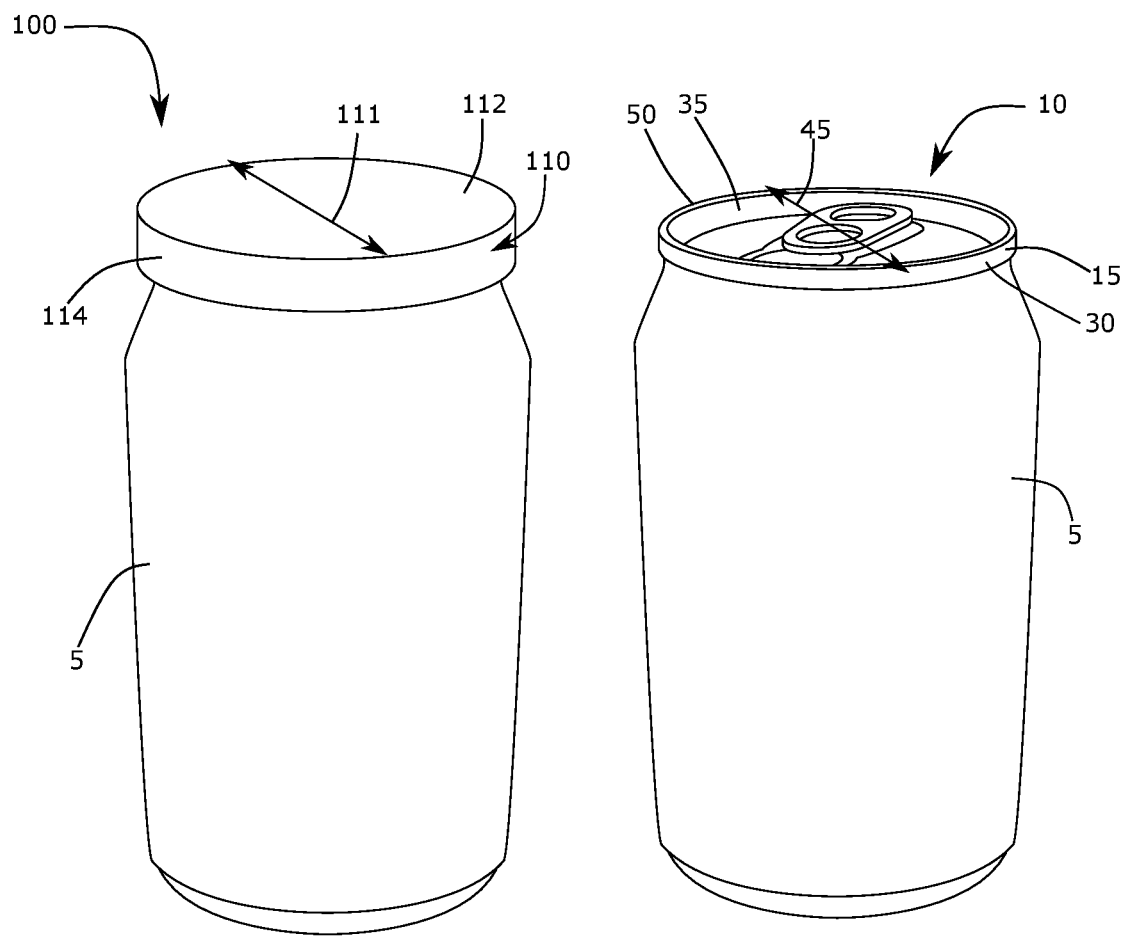
FIG. 3 is a perspective view of the device of FIG. 1, illustrating the device attached to the top of the beverage can, and a beverage can with no device attached to illustrate the top of the beverage can, according to an embodiment of the present disclosure.
Figure 4:
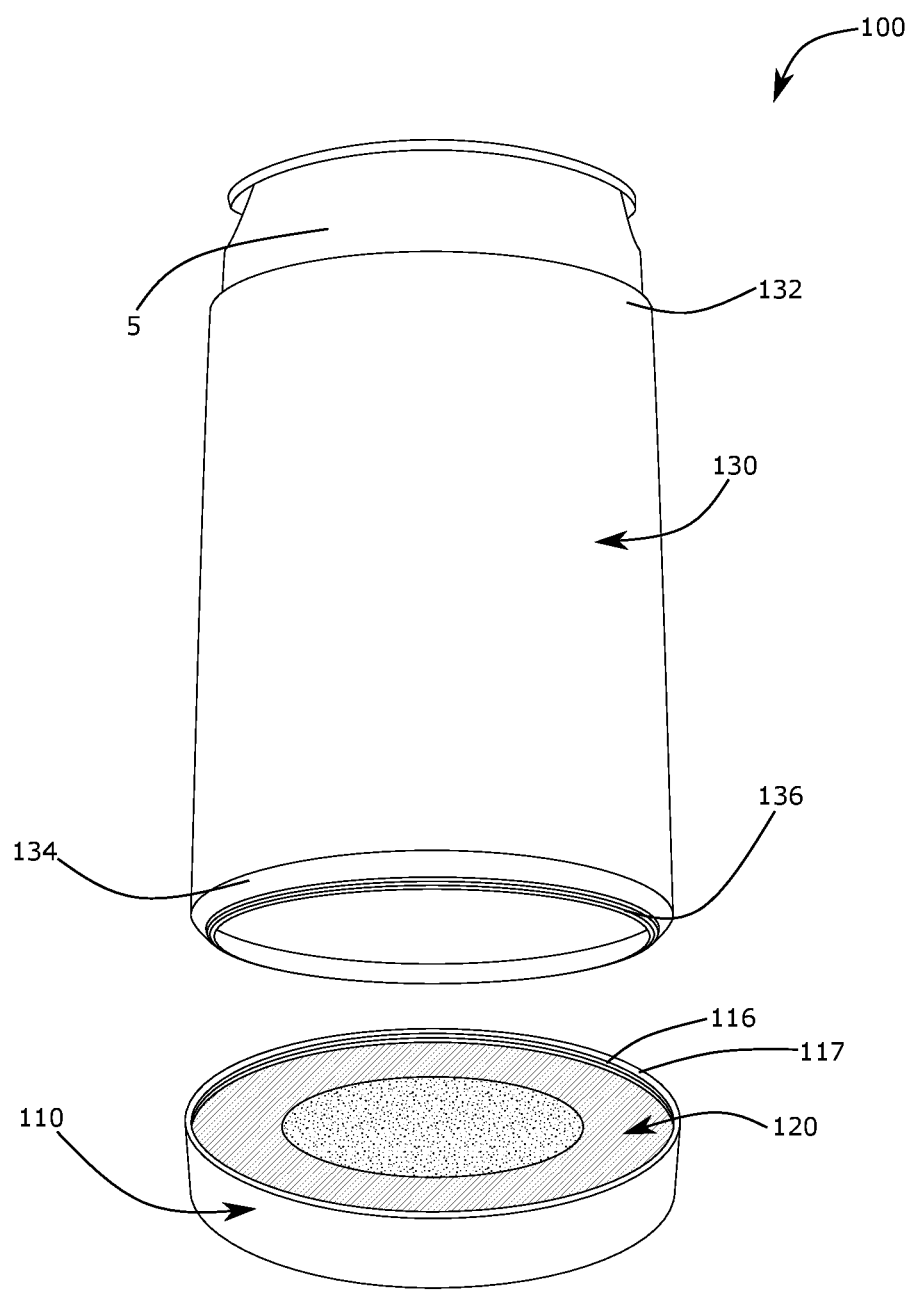
FIG. 4 is a perspective view of the device, illustrating a beverage can holder and the device being configured to attach to the beverage can holder, according to another embodiment of the present disclosure.
Figure 5:
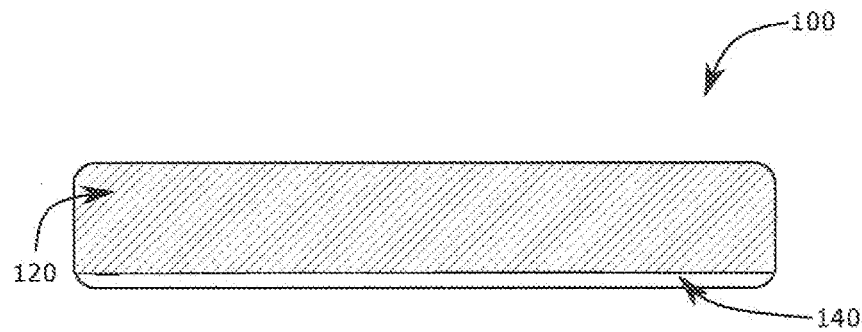
FIG. 5 is a side view of the device of FIG. 1, illustrating a cleaning-member of the device removed from a main-body of the device and including a pouch-means at a bottom thereof, according to an embodiment of the present disclosure.

Further, in some embodiments, the device 100 may include an attachment means 116 configured to removably attach the device 100 to at least one of the top 10 and a bottom 40 of the beverage can 5. For example, the attachment means 116 may be located on an inner surface 117 of the bordering-wall 114 of the main-body 110 that is configured to mate with top 10 or the bottom 40 of the beverage can 5. In some embodiments, the attachment means 116 may be configured to mate with the circumferential lip 25 of the beverage can 5 to attach the device 100 to the top 10 of the beverage can 5; or mate with a bottom-lip on the bottom 40 of the beverage can 5 to attach the device 100 thereto. As such, the attachment means 116 may be a thread, such as a female thread, a groove for receiving the lip(s), a snap fastener, or the like. The device 100 in FIG. 2A is shown to be transparent for illustration of the attachment means 116. In this figure, the attachment means 116 is a snap fastener configured to mate with the circumferential lip 25 of the beverage can 10. It is contemplated that the attachment means 116 may be universal so as to attach the device 100 to any sized/shaped beverage can 5.

Additionally, as shown, a beverage can holder 130 may be provided and the attachment means 116 may be configured to removably attach the device 100 to at least one of a top 132 and a bottom 134 of the beverage can holder 130. This may be additional to, or instead of attaching to the beverage can 5. The beverage can holder 130 may be an insulated receptacle. The beverage can holder 130 may be provided with the device 100. In this embodiment, the beverage can holder 130 may include a mating-attachment 136 specifically configured to mate with the attachment means 116 on the device 100. For example, the attachment means 116 may be a female thread, and the matching-attachment 136 may be a male thread. In other embodiments, the attachment means 116 may be universal as above, such that the device 100 may be attached to any beverage can holder 130.

As shown, the cleaning-member 120 may be removably seated within the interior 115. In some embodiments the cleaning-member 120 be permanent to the device 100, and in other embodiments the cleaning-member 120 may be disposable and therefore may be replaced with a new cleaning-member 120 after use (either single-use or after a certain amount of uses). Further, the cleaning-member 120 may include an absorbent material. In some embodiments, the absorbent material may be a sponge material. Further, in some embodiments, the cleaning-member 120 may include a cloth material. For example, the cleaning-member 120 may be made from the sponge material and may be covered, at least partially, with the cloth material.

The cleaning-member 120 may include an inner-section 122 and an outer-section 124. The inner-section 122 may be sized and configured to clean the top-wall 15 of the beverage can 5. For example, the inner-section 122 may include an inner section-diameter 127 substantially equal to a top wall-diameter 55 of the top-wall 15 of the beverage can 5. Further, the outer-section 124 may be sized and configured to clean an outer surface 30 and an inner surface 35 of the circumferential lip 25 of the beverage can 5. In this embodiment, the outer-section 124 may be wider than the circumferential lip 25 to ensure that both the outer surface 30 and the inner surface 35 are thoroughly cleaned. Preferably, both the inner-section 122 and the outer-section 124 maybe of a thickness configured to maximize contact with the top 10 of the beverage can 5 such that when the device 100 is pressed over the top of the beverage can 5, the inner-section 122 is placed in full contact with the top-wall 15 and the outer-section 124 is placed in full contact with the outer surface 30, the inner surface 35 and a top surface 50 of the circumferential lip 25.

At least one of the inner-section 122 and the outer-section 124 may be saturated with a cleaning composition 126. Preferably, both the inner-section 122 and the outer-section 124 may be saturated with the cleaning composition 126. The cleaning composition 126 may be configured to disinfect and/or sanitize the top 10 of the beverage can 5, and thereby may at least substantially reduce, if not kill or inactivate, pathogenic matter located on the top of the beverage can 5, such as bacteria, viruses, fungi, and the like.

Figure 6:
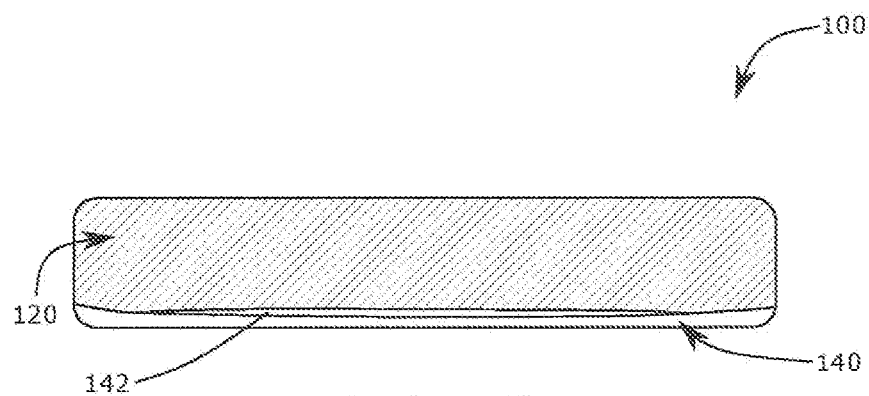
FIG. 6 is a side view of the device of FIG. 5, illustrating the pouch-means including a pouch-opening, according to an embodiment of the present disclosure.
Figure 7:
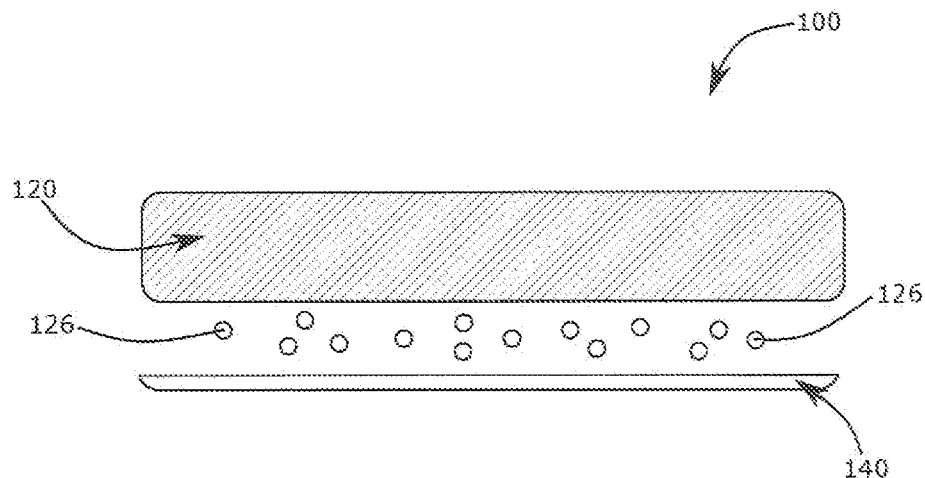
FIG. 7 is an exploded side view of the device of FIG. 5, illustrating the cleaning-member, a cleaning composition, and the pouch-means, according to an embodiment of the present disclosure.
Figure 8:
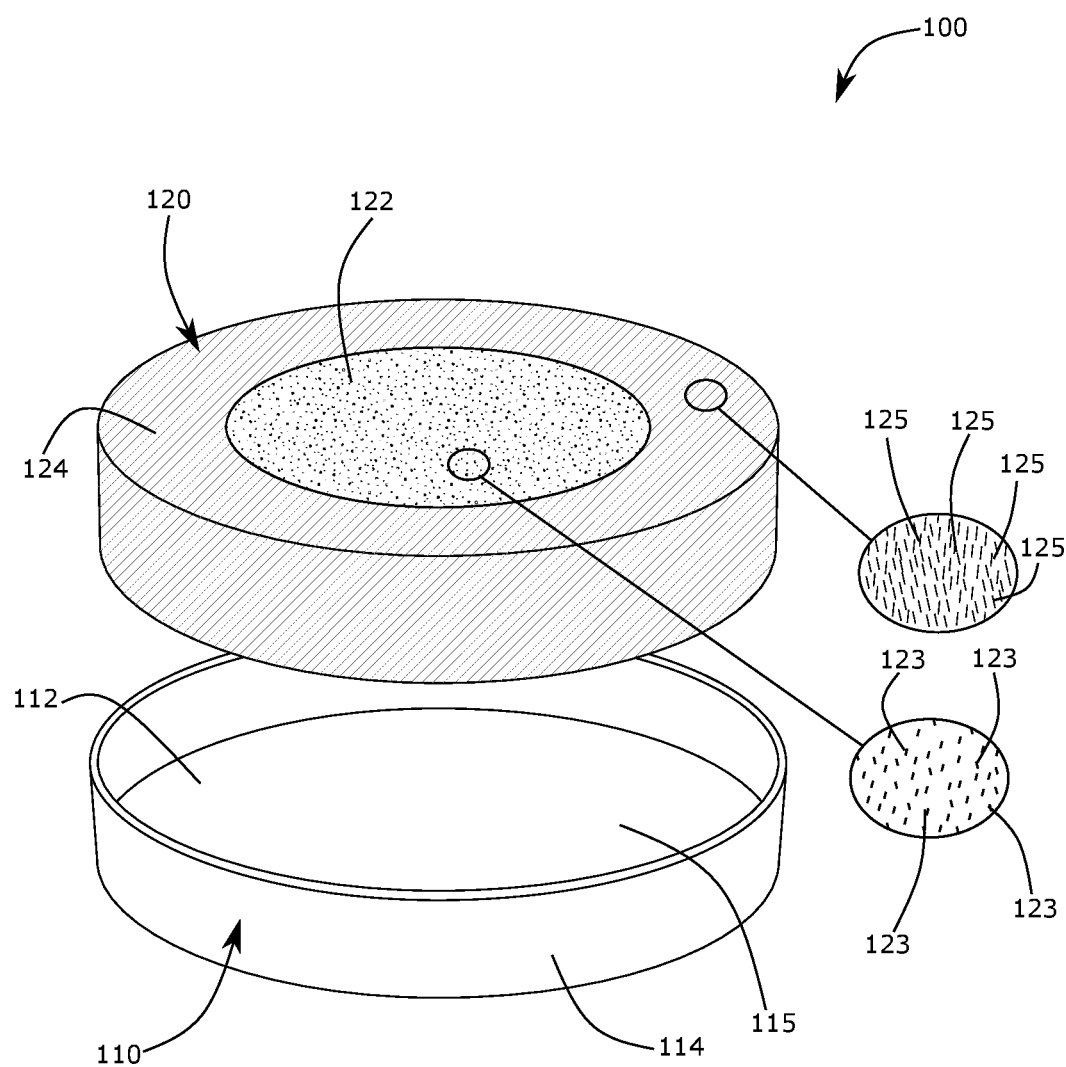
FIG. 8 is a front perspective view of the device, illustrating the cleaning-member removed from the main-body and illustrating bristles located on the cleaning-member, according to an embodiment of the present disclosure.
Figure 9:
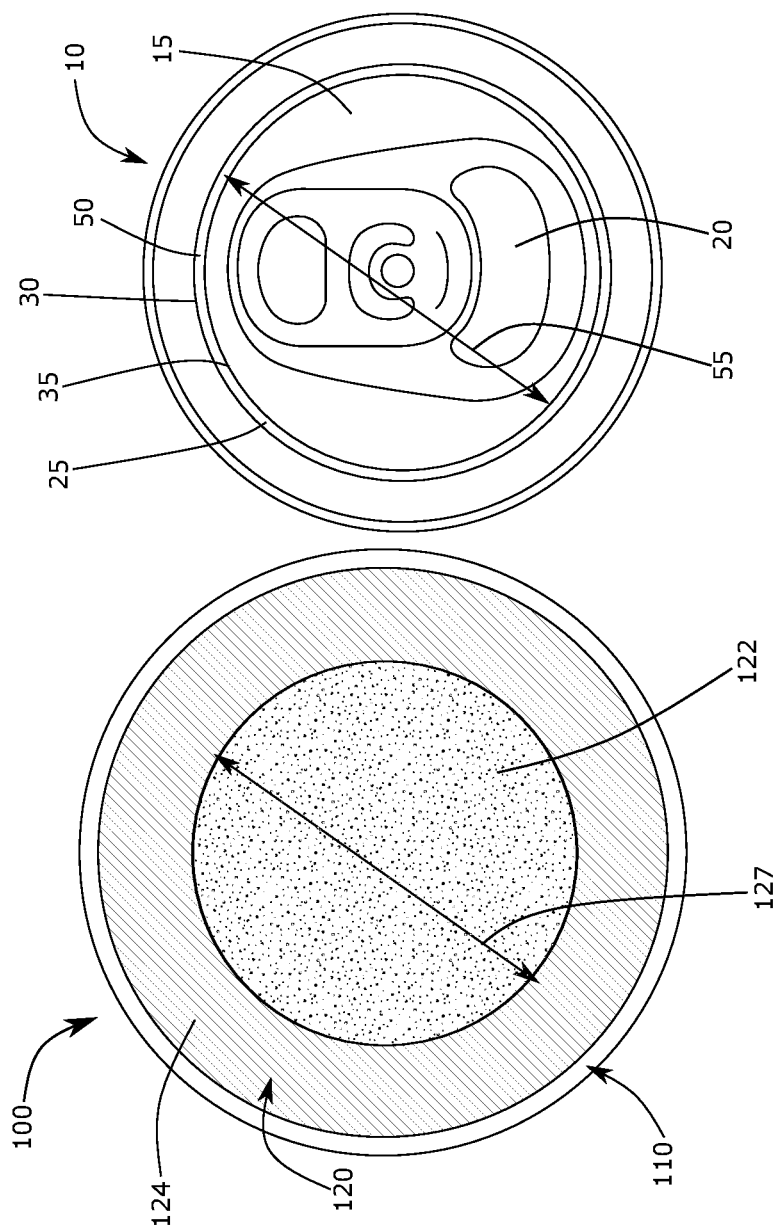
FIG. 9 is a top view of the device, illustrating a size of the cleaning-member compared to a size of the top of the beverage can, according to an embodiment of the present disclosure.

In some embodiments, a pouch-means 140 may be provided with the device 100. The pouch-means 140 may be configured to hold a predetermined amount of the cleaning composition 126. The pouch-means 140 may be selectively refilled with the cleaning composition 126. To facilitate this, the pouch-means 140 may include a pouch-opening 142 for receiving the cleaning composition 126, as illustrated in FIG. 6. In some embodiments, the cleaning composition 126 may be easily poured, inserted, applied, etc. to the pouch-means 140. It should be appreciated that the way in which the cleaning composition 126 is shown in FIG. 7 is for illustrative purposes. Various states of matter are contemplated for the cleaning composition 126, such as liquid, gel, paste, etc.

Preferably, the pouch-means 140 may be permanently attached to the cleaning-member 120, however it is contemplated that in some embodiments the pouch-means 140 may be removable. In some embodiments, as shown, the pouch-means 140 may be attached to a bottom of the cleaning-member 120. The pouch-means 140 may be configured to place the cleaning-member 120 in communication with the cleaning composition 126 to saturate the at least one of the inner-section 122 and the outer-section 124 with the cleaning composition 126. Again, preferably the inner-section 122 and the outer-section 124 may both be saturated with the cleaning composition 126. As above, the cleaning-member 120 may be made from the absorbent material. Preferably, the absorbent material may prevent the top 10 of the beverage can 5 from becoming too wet when it is cleaned with the device 100.

In some embodiments, the cleaning composition 126 may include alcohol such as ethyl alcohol, isopropyl alcohol, or the like. In this embodiment, the cleaning composition 126 may include a concentration of the alcohol configured to at least substantially reduce the pathogenic matter located on the top of the beverage can 5. For instance, the cleaning composition 126 may include between 60-80 % percent alcohol. It should be appreciated that the cleaning composition 126 is not limited to alcohol however, and other sanitization/disinfectant substances and agents are also contemplated.

Further, to aid in cleaning of the top of the beverage can 5, the outer-section 124 may include a first plurality of bristles 125. The first plurality of bristles 125 may include an abrasive texture to thoroughly scrub the top 10 of the beverage can 5. Further, the first plurality of bristles 125 may be stiff and thin enough for easy insertion into a groove between the circumferential lip 25 and the top-wall 15, and a groove between where the circumferential lip 25 meets the beverage can 5.

In addition to this, at least a portion of the inner-section 122 may include a second plurality of bristles 123. The portion of the inner-section 122 that includes the second plurality of bristles 123 may substantially align with the mouth-section 20 of the beverage can 5 when the device 100 is atop the beverage can 5. This may allow the second plurality of bristles 123 to specifically clean the mouth-section 20. To aid in this cleaning, the second plurality of bristles 123 may further include the abrasive texture. In other embodiments, an entirety of the inner-section 122 may include the second plurality of bristles 123. The first plurality of bristles 125 and the second plurality of bristles 123 may be made from the same material in some embodiments or may be made from different material in other embodiments. Further, in some embodiments, the inner-section 122 and the outer-section 124 may be made from the same materials, or in other embodiments, the inner-section 122 and the outer-section 124 may be made from different materials.

In some embodiments, the device 100 may be integrated into other devices, furniture, etc. or may be configured for multiple uses. For example, the device 100 may be integrated into tables or tabletops (not illustrated), chairs (not illustrated), beverage holders (as above), beverage cans (as above), coasters (not illustrated) or the like. Alternatively, the device may be used as a coaster. For example, the device 100 may be placed on a surface such that the plate 112 of the main-body 110 may be used as a coaster. Further, the device 100 may also be configured for easy portability, and as such, may include means for aiding in the portability thereof. For instance, as above, the device may include a keyring for attaching the device to keychains.

Figure 10:
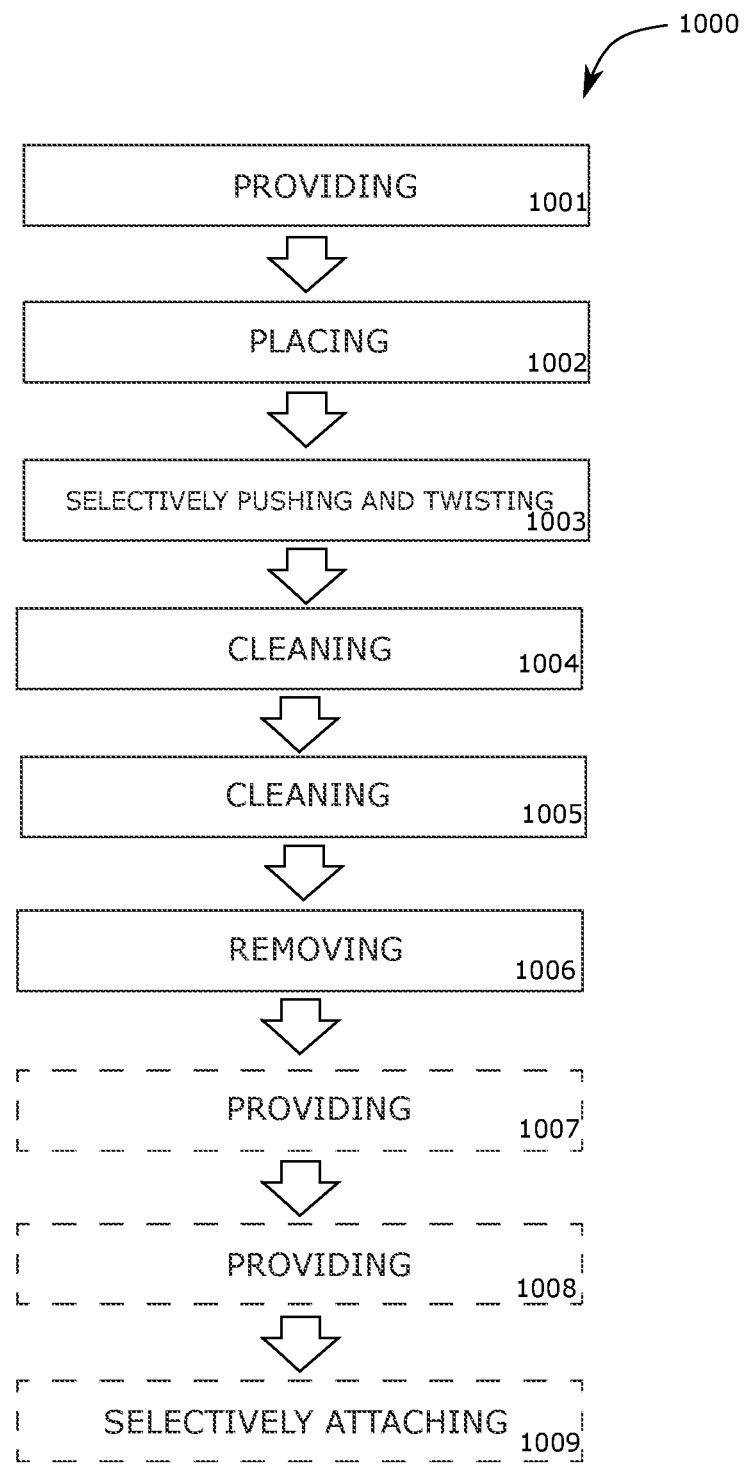
FIG. 10 is a flow diagram illustrating a method of using a device for cleaning a top of a beverage can, according to an embodiment of the present disclosure.

Referring now to FIG. 10 showing a flow diagram illustrating a method of using a device for cleaning a top of a beverage can ("method" 1000) according to an embodiment of the present disclosure. In particular, the method 1000 may include one or more components or features of the device 100 as described above. As illustrated, the method 1000 may include the steps of: providing 1001 the device as above; placing 1002 the main-body over the top of the beverage can, the cleaning-member being seated therewithin; selectively pushing and twisting 1003 the main-body over the top of the beverage can, thereby: cleaning 1004 the top-wall of the beverage can with the inner-section of the cleaning-member and cleaning 1005 the outer surface and the inner surface of the circumferential lip of the beverage can with the outer-section of the cleaning-member; and removing 1006 the device from the top of the beverage can to drink a contents thereof. Further steps may include providing 1007 the device wherein the device further includes the attachment means; providing 1008 the beverage can holder; and selectively attaching 1009 the device to one of the beverage can and the beverage can holder.

It should be noted that steps 1007, 1008 and 1009 are optional steps and may not be implemented in all cases. Optional steps of method 1000 are illustrated using dotted lines in FIG. 10 so as to distinguish them from the other steps of method 1000. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for cleaning a top of a beverage can are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. An apparatus for cleaning a top of a beverage can, the beverage can having a cylindrical body and a top, the top of the beverage can including a top-wall having an open-able mouth section therein, and an upwardly extending circumferential lip bordering the top-wall, the apparatus comprising:
   a beverage can holder having a cylindrical body, a closed bottom and an open top defining an interior, the beverage can holder configured to removably receive the beverage can within the interior; and
   a cleaning device having a cleaning composition configured to disinfect and sanitize the top of the beverage can, the cleaning device having a main-body including a plate and a bordering-wall defining an interior, the main-body sized to encompass the top of the beverage can; and
   a cleaning-member removably seated within the interior of the cleaning device, the cleaning-member including an inner-section and an outer-section, the inner section being sized and configured to clean the top-wall of the beverage can, the outer-section being sized and configured to clean an outer surface and an inner surface of the circumferential lip of the beverage can, at least one of the inner-section and the outer-section being saturated with the cleaning composition, the cleaning device removably attachable to the exterior of the bottom of the beverage can holder when the cleaning device is not in use.

2. The apparatus of claim 1, further comprising a pouch-means configured to hold a predetermined amount of the cleaning composition, wherein the pouch-means is attached to the cleaning-member, and wherein the pouch-means is configured to place the cleaning-member in communication with the cleaning composition to saturate said at least one of the inner-section and the outer-section with the cleaning composition.

3. The apparatus of claim 2, wherein the cleaning-member includes an absorbent material.

4. The apparatus of claim 3, wherein the absorbent material is a sponge material.

5. The apparatus of claim 4, wherein the outer-section includes a first plurality of bristles.

6. The apparatus of claim 5, wherein at least a portion of the inner-section includes a second plurality of bristles.

7. The apparatus of claim 6, wherein the portion including the second plurality of bristles substantially aligns with the mouth-section of the beverage can when the device is atop the beverage can.

8. The apparatus of claim 7, wherein at least one of the first plurality of bristles and the second plurality of bristles include an abrasive texture.

9. The apparatus of claim 8, wherein both the inner-section and the outer-section are saturated with the cleaning composition.

10. The apparatus of claim 9, wherein the cleaning composition includes alcohol.

11. The apparatus of claim 10, wherein the cleaning composition includes a concentration of said alcohol configured to at least substantially reduce pathogenic matter located on the top of the beverage can.

12. The apparatus of claim 1, wherein the main-body includes a body-diameter slightly larger than a can-diameter of the top of the beverage can.

13. The apparatus of claim 12, wherein the apparatus includes an attachment means configured to removably attach the cleaning device to at least one of the top and a bottom of the beverage can holder.

14. The apparatus of claim 1, wherein the cleaning device having a female thread attachment and the bottom of the beverage can holder having a male thread attachment is configured to receive the female thread attachment of the cleaning device, whereby the cleaning device is removably attachable to the bottom of the beverage can holder when not in use.

* * * * *